(12) United States Patent
Cho et al.

(10) Patent No.: US 8,039,790 B2
(45) Date of Patent: Oct. 18, 2011

(54) PHANTOMS AND METHODS FOR VERIFICATION IN RADIOTHERAPY SYSTEMS

(75) Inventors: Young-Bin Cho, Mississauga (CA); Mohammad Islam, Oakville (CA); Monique van Prooijen, Mississauga (CA); David Jaffray, Etobicoke (CA); Mark Taylor, Toronto (CA)

(73) Assignee: University Health Network, Toronto, Ontario (CA)

( * ) Notice: Subject to any disclaimer, the term of this patent is extended or adjusted under 35 U.S.C. 154(b) by 0 days.

(21) Appl. No.: 12/780,460

(22) Filed: May 14, 2010

(65) Prior Publication Data
US 2010/0288916 A1 Nov. 18, 2010

Related U.S. Application Data

(60) Provisional application No. 61/178,327, filed on May 14, 2009.

(51) Int. Cl.
*G01D 18/00* (2006.01)
(52) U.S. Cl. ..................................................... 250/252.1
(58) Field of Classification Search ............... 250/252.1, 250/370.01–370.16, 363.01–363.1, 393; 378/207
See application file for complete search history.

(56) References Cited

U.S. PATENT DOCUMENTS

| 4,931,653 A | 6/1990 | Hamm et al. |
|---|---|---|
| 5,006,714 A | 4/1991 | Attix |
| 5,793,835 A | 8/1998 | Blanck |
| 6,345,114 B1 | 2/2002 | Mackie et al. |
| 6,712,508 B2 | 3/2004 | Nilsson et al. |
| 6,904,162 B2 | 6/2005 | Robar et al. |
| 7,142,634 B2 | 11/2006 | Engler et al. |
| 7,510,325 B2 | 3/2009 | Endo et al. |
| 7,636,419 B1 | 12/2009 | Nelson |
| 2003/0004503 A1 | 1/2003 | Nilsson et al. |
| 2003/0219098 A1* | 11/2003 | McNutt et al. ................... 378/65 |
| 2005/0109939 A1 | 5/2005 | Engler et al. |
| 2007/0020793 A1 | 1/2007 | Adamovics |
| 2009/0250618 A1 | 10/2009 | Simon |
| 2009/0296893 A1 | 12/2009 | Strobel |
| 2009/0310845 A1 | 12/2009 | Ogawa et al. |
| 2010/0074414 A1 | 3/2010 | Katsuda et al. |

FOREIGN PATENT DOCUMENTS

| EP | 0608237 | 1/1993 |
|---|---|---|
| EP | 1887790 A1 | 2/2008 |
| WO | 0025678 | 5/2000 |
| WO | 02100477 A2 | 12/2002 |
| WO | 2004079393 A2 | 9/2004 |

(Continued)

OTHER PUBLICATIONS

Suchowerska et al., "Directional dependence in film dosimetry: radiographic and radiochromic film," 2001, Physics in Medicine and Biology, vol. 46, pp. 1391-1397.*

(Continued)

*Primary Examiner* — Kiho Kim
(74) *Attorney, Agent, or Firm* — Norton Rose OR LLP (57) ABSTRACT

Methods and phantoms for verification in radiotherapy systems. A phantom for verification in a radiotherapy system may include a body to support a detector surface for obtaining a panoramic image of individual radiation beams in the radiotherapy system. The detector surface may be positioned in an intermediate region between the one or more sources and a target isocenter of the radiotherapy system. The detector surface may at least partially surround the target isocenter.

24 Claims, 9 Drawing Sheets

FOREIGN PATENT DOCUMENTS

| | | |
|---|---|---|
| WO | 2008098591 | 8/2008 |
| WO | 2009004297 A2 | 1/2009 |
| WO | 2009120494 A2 | 10/2009 |

OTHER PUBLICATIONS

Higgins et al., "Fractionated stereotactic radiotheraphy for pediatric patients with retinobastoma," 2006, Journal of Applied Clinical Medical Physics, vol. 7, No. 2, pp. 9-17.*

Rink et al., "Suitability of radiochromic medium for real-time optical measurements of ionizing radiation dose," 2005, Medical Physics, vol. 32, No. 4, pp. 1140-1155.*

Vatnitsky et al., "Radiochromic film dosimetry for verification of dose distributions delivered with proton-beam radiosurgery," 1997, Physics in Medicine and Biology, vol. 42, pp. 1887-1898.*

Zeidan et al., "Characterization and use of EBT radiochromic film for IMRT dose verification,", 2006, Medical Physics, vol. 33, No. 11, pp. 4064-4072.*

Maitz, Ann H, et al., "Quality Assurance for Gamma Knife Stereotactic Radiosurgery", Int. J. Radiation Oncology Biol. Phys., vol. 32, No. 5. pp. 1465-1471, 1995, USA.

* cited by examiner

PHANTOMS AND METHODS FOR VERIFICATION IN RADIOTHERAPY SYSTEMS

CROSS-REFERENCE TO RELATED APPLICATIONS

The present disclosure claims priority from U.S. provisional application No. 61/178,327, filed May 14, 2009, the entirety of which is hereby incorporated by reference.

TECHNICAL FIELD

The present disclosure relates generally to phantoms and methods for verification in radiotherapy systems. In particular, the present disclosure relates to phantoms and methods for verification of source configuration and dosages in such systems.

BACKGROUND

Stereotactic radiosurgery (SRS) has been the treatment of choice for patients with brain tumors[1-3] or functional disorders.[4,5] For example, the Leksell Gamma Knife (LGK) (Elekta, Norcross, Ga.) has been used successfully to deliver a high dose to small target volumes by focusing 201 $^{60}$Co sources placed in a nearly complete hemispherical arrangement to one point. For the LGK model 4C, the size of the high dose volume delivered by one shot is determined by one of four possible collimator helmets with collimators ranging in size from 4 to 18 mm in diameter. The new model of the LGK system, Perfexion™ (PFX), adopts technical innovations that include eight independent position-controlled source modules (sectors) and a stationary built-in collimator system with three apertures for each source corresponding to 4, 8, and 16 mm field sizes. Thus, a single shot may simultaneously include multiple collimator sizes. The new system eliminates the need for time consuming manual installation of collimator helmets as in the older models of LGK and moves sources in sectors over the planned aperture positions in the collimator. This new technology has led to a possible improvement in efficiency in treatment planning, delivery, and workflow.[6,7]

Radiosurgery, characterized by a single high dose fraction, requires regular and careful quality assurance (QA).[8] Checking the integrity of collimator systems is one of the important physics QA items required to ensure the accuracy of dose delivery. Although a simple visual inspection was sufficient for checking the geometrical configuration of the collimators in older versions of LGK, there is no easy way to independently evaluate the built-in collimator of the PFX. The conventional method of exposing a film at the isocenter provides a composite dose image, which has been successfully used for checking coincidence between the radiation and mechanical isocenters and also for dose rate verification. However, it is difficult to interpret the film in terms of the integrity of each individual source and corresponding collimator system. Maitz et al.[8] used sequential strips of film around a spherical phantom with a 4 mm diameter lead ball at the center of the phantom. Images of the lead ball were identified within each exit image of the beam to verify the source-collimator alignment.

It may be useful to have a system and method of verifying the geometric configuration of the source and collimator modules of a radiosurgery system, such as a stereotactic radiosurgery system, or a radiotherapy system.

SUMMARY

In some aspects, there is provided a phantom for verification in a radiotherapy system comprising: a body configured to support a detector surface for obtaining a panoramic image of individual radiation beams produced by one or more sources in the radiotherapy system; wherein the body is configured to position the detector surface for obtaining the panoramic image in an intermediate region between the one or more sources and a target isocenter of the radiotherapy system.

In some aspects, there is provided a method of verification in a radiotherapy system, the method comprising: obtaining a panoramic image of individual radiation beams in the radiotherapy system, the panoramic image being indicative of locations of individual beams produced by one or more sources in the radiotherapy system; and calculating at least one of source configuration and radiation dosage, based on the beam images of the panoramic image, for verification with a respective pre-determined target configuration or target dosage.

BRIEF DESCRIPTION OF THE DRAWINGS

Reference will now be made to the drawings, which show by way of example embodiments of the present disclosure, and in which.

DETAILED DESCRIPTION

The conventional method of exposing a film at the isocenter for verification of a radiotherapy system may have disadvantages, such as difficulty in verifying each individual source and corresponding collimator system. For example, in Maitz et al.[8], the coincidence of beams with the isocenter was of primary interest. The metal ball at the isocentre was imaged at the exit beam surface of the phantom. This method may be limited in its ability to verify simultaneously all the sources and corresponding collimator configurations, as well as determining the peripheral dose. In Maitz, use of a high contrast object is necessary, to determine whether a source is focusing at the target isocenter. Maitz relies on exit beams passing through the imaged phantom. Maitz addresses only relatively limited geometrical aspects of the system and relies on using multiple small pieces of film. It may be desirable to address one or more of the disadvantages of these conventional methods.

The present disclosure describes phantoms and methods for verification in radiotherapy systems, particularly verification of source configuration and/or dosages in such systems. The radiotherapy system may be a radiosurgery system, such as a stereotactic radiosurgery system. In general, radiosurgery is a form of radiotherapy and all discussion herein with respect to radiotherapy systems may equally apply to radiosurgery systems. The disclosed methods and phantoms may also be used for verification of linear accelerator-based treatments, particularly in intensity-modulated radiation therapy (IMRT) or arc therapy modes. In general, the disclosed methods and phantoms may be suitable for radiotherapy systems using one or more sources to produce beams from various directions and various field shapes. The methods and phantoms may be suitable for verification (e.g., treatment plan verification or commissioning) of a radiotherapy system, including a system in which a radiation therapy source is controlled by a robotic arm, as in the CyberKnife radiosurgery system (Accuray, Sunnyvale, Calif.) or a system having multiple static radiation sources, as in the Gamma Knife system. This may provide verification of treatment plans from any suitable radiotherapy system, including linear accelerator systems.

Conventional methods of radiotherapy system verification may provide only information about the dose at a single point or location (e.g., the isocenter) within the system and may not provide any information about individual sources or beams produced by the sources in the system. Conventional methods may also be unable to verify dosage plans that have relatively complex 3D shapes or may be unable to account for peripheral or surface dosage.

In some aspects, a method of verification in a radiotherapy system may comprise: obtaining a panoramic image of individual radiation beams in the radiotherapy system, the panoramic image being indicative of locations of individual beams produced by one or more sources in the radiotherapy system; and calculating at least one of source configuration and radiation dosage, based on the beam images of the panoramic image, for verification with a respective pre-determined target configuration or target dosage.

By "panoramic", it is meant that the single image shows multiple or all individual beams impacting (e.g., entering or exiting) a surface. The panoramic image may be obtained for a surface that is in an intermediate region between the sources in the radiotherapy system and the intended isocenter or target isocenter of the system. The panoramic image may be from a surface (e.g., a 3D surface) at least partially surrounding the isocenter. Thus, the panoramic image may be indicative of individual beams from the sources in the intermediate space rather than at the isocenter of the system.

Verification of source configuration may be useful for commissioning and/or quality assurance of the radiotherapy system, for example at the time of installation, and when in use (e.g., daily, monthly or yearly quality assurance checks). This method may allow for verification of parameters such as those related to radiation dose delivery system integrity (e.g., source viability, source alignment, and spatio-temporal accuracy of the collimator system), and those related to positioning system integrity (e.g., frame alignment, and couch positioning) among others.

In some aspects, the disclosed methods and phantoms may be useful for verifying a setting for a radiotherapy system (e.g., for a planned dosage or treatment plan). The planned dosage may also be verified. Using this verification, a particular treatment plan may be verified. For example, a treatment plan may be designed to deliver a volumetric dose at certain locations within a phantom or patient. This treatment plan may include settings for the radiotherapy system designed to produce the desired dose. Using the disclosed methods and phantoms, the system settings according to the treatment plan may be applied to a phantom to obtain a 2D panoramic image, and the volumetric dose may be calculated based on the 2D image. This calculated volumetric dose may be compared to the desired or intended dose for the patient in order to verify the settings for the treatment plan.

In some examples, the panoramic image may be obtained by using a phantom configured for verification of radiotherapy systems. The phantom may include a body that supports a detector surface that produces the panoramic image described above. In the present disclosure, the term "detector surface" may be used to refer to any surface, which may be planar or non-planar, capable of detecting beams produced by sources in the radiotherapy system. A detector surface may be a radiochromic or radiographic film, a fluorescent or solid state screen, or any other suitable surface that is capable of detecting radiation beams. A detector surface may be selected to be more sensitive to radiation to provide greater contrast gradient in the panoramic image produced. The detector surface may be supported at an intermediate region between the sources and the isocenter of the radiotherapy system, in order to obtain a panoramic image of individual beams from the sources. The body of the phantom may shape the detector surface into a particular geometry, including, for example, at least partially conforming to a substantially cylindrical, cubical, conical or spherical geometry.

Figure 1:
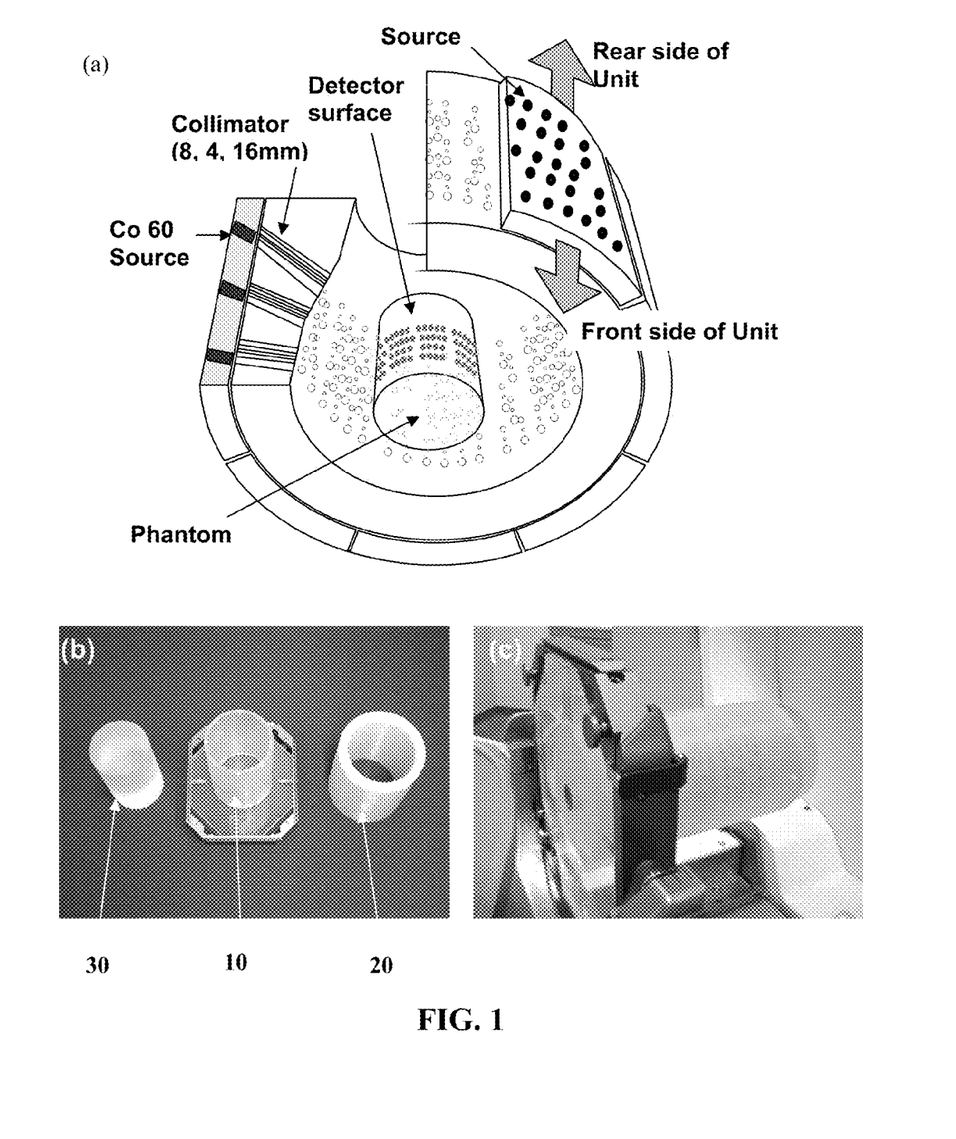
FIG. 1 shows an example phantom suitable for verification in a radiotherapy system and its use in an example radiotherapy system.

The phantom may include an outer sleeve that holds the detector surface against an outer surface of the body and causes the detector surface to conform to an outer geometry of the body. Similarly or in addition, the phantom may include an inner core that holds the detector surface against an inner surface of the body and causes the detector surface to conform to an inner geometry of the body. For example, as shown in FIG. 1b), the phantom may include a hollow cylindrical body 10, a cylindrical outer sleeve 20 and a cylindrical inner core 30. Although only one sleeve is shown, the phantom may include a plurality of nesting sleeves. Where there are multiple nesting sleeves and/or where the core is used together with one or more sleeves, nesting layers of multiple detector surfaces may be mounted on the surfaces of respective nesting sleeves and/or the core, such that multiple panoramic images can be obtained simultaneously at different distances from the isocenter.

The panoramic image obtained by the detector surface shows individual radiation beams produced by one or more sources in the radiotherapy system. The image is obtained in an intermediate region between the sources and the target isocenter of the system, and may be indicative of the entrance beams to (i.e., beams travelling towards) and/or exit beams from (i.e., beams travelling away from) the phantom. For example, the detector surface may be positioned in an upper portion of the treatment area in the system, such that only entrance beams are imaged. Because the panoramic image indicates individual beams, the individual configurations and/or locations of the one or more sources may be calculated, as well as the dosage provided by the summation of the individual beams in the treatment area.

The methods and phantoms disclosed here may provide information about the surface dose as experienced by the detector surface. Surface dose in the area of beam entrance may be considered similar to fluence measurement in intensity modulated radiation therapy, which is a frequently used patient specific quality assurance test. In the case of rotational therapy, a panoramic image may provide composite fluence in a single sheet of film or detector surface. The disclosed methods and phantoms may be utilized for a patient-specific QA of radiotherapy (e.g., radiosurgery, such as using Gamma knife) treatment and rotational radiation therapy by comparing the surface dose in the area of beam entrance (fluence) with the fluence computed from the planning system.

In some example embodiments, the phantom is cylindrical in shape, and a radiochromic film may be wrapped around the outside or inside of the phantom. In general, the phantom may be configured to allow a detector surface (e.g., a radiochromic film) to be fastened to it in a panoramic manner, exposing the film to radiation sources from a plurality of directions.

The panoramic image of the sources may be used for verification in a radiotherapy system in various ways. For example, using equations commonly available (e.g., equations used in treatment planning), the image of the source beam locations and/or dimensions may be used to calculate, for example, the configuration of the sources; the dose delivered at the intended treatment center; the peripheral dose in areas peripheral to the treatment center; and/or the dose distribution on the surface of an intended patient (i.e., surface dosage). Other such calculations may be possible using variations of existing equations and techniques.

This disclosure also includes software and algorithms for carrying out at least part of the above methods. These software and algorithms may be provided in the form of computer products having computer executable instructions tangibly recorded thereon for carrying out the methods described above for verification in a radiotherapy system.

In some examples, the disclosed methods and phantoms for verification may also include verification of dosage at the isocenter of the system. For example, the phantom described above may be configured to include or accommodate a radiation detector localized at the isocenter, for measuring the reference dose rate at the isocenter. Suitable radiation detectors may include, for example, ion chambers, films and gel dosimeters. Thus, the verification may include both verification based on 2D measurements from an intermediate surface as described above as well as verification based on a 3D measurement at the isocenter. This may allow for a comprehensive dosimetric quality assurance of the radiotherapy system by providing simultaneous dosimetry at the isocenter as well as at peripheral or intermediate locations. This may provide an all-in-one quality assurance method and phantom for the radiotherapy system, and may help improve the efficiency and/or reliability of such quality assurance measurements.

Although the phantom has been described as being configured to support a detector surface in a cylindrical configuration, it should be understood that any geometry may be used for the detector surface, with corresponding adaptations for the phantom. For example, while a cylindrical phantom may support a cylindrical detector surface, other phantom geometries may be used for corresponding detector surface geometries. In some examples, the phantom may be of conical, cubical or spherical shape, to support detector surfaces that are correspondingly conical, cubical or spherical, respectively. Other geometries may be possible, including both regular and irregular surface geometries. The phantom geometry may be configured to ensure that the phantom may be relatively accurately and reproducibly positioned for imaging and dose delivery, and that the detector surface can be mounted or otherwise held fixed by the phantom. With appropriate geometrical shapes, verification may be extended to perform quality assurance and/or dosimetry tests for other forms of stereotactic radiation therapy, for example including therapy provided by the CyberKnife system or the Gamma Knife system.

Although a radiographic or radiochromic film has been described as the detector surface for capturing the panoramic image, any other suitable detector may be used. For example, any surface imaging devices may be used, including other types of films, fluorescent screens or solid state screens (e.g., flexible or non-flexible, contiguous or discrete). In some examples, a flexible solid state imaging panel may be used as the detector surface and may provide panoramic images that may be captured and/or analyzed on-line or in real-time.

Figure 9A:
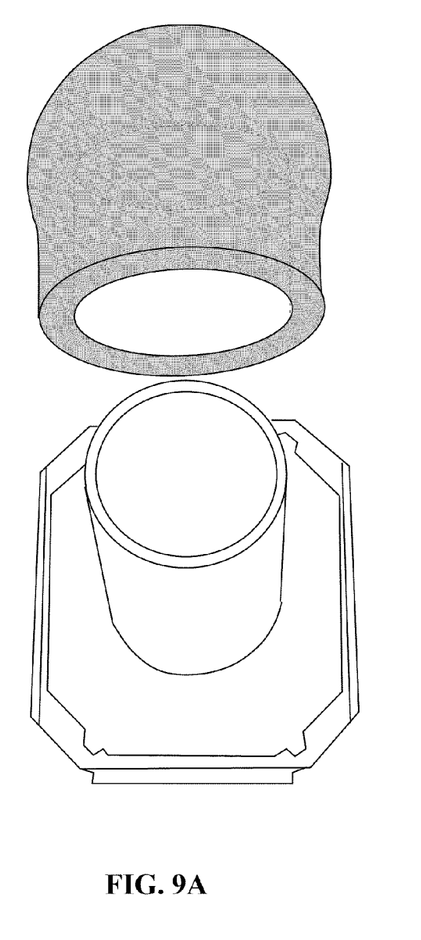
FIGS. 9A and 9B illustrate examples of phantoms with inserts to facilitate depth-helmet measurements.
Figure 9B:
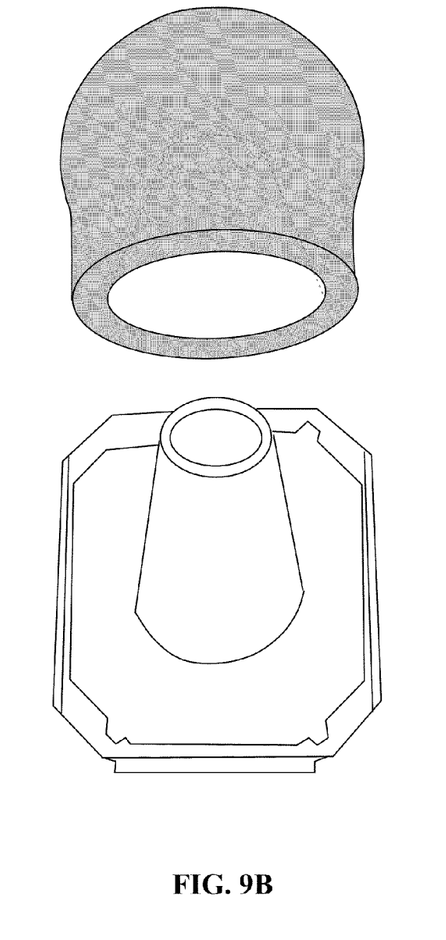

In some examples, the phantom may be configured to allow simultaneous testing of the calculation geometry and dosimetry for comprehensive commissioning of a treatment planning system for a radiotherapy system. For example, the phantom may be configured to accommodate or include an insert to facilitate depth-helmet measurements. The insert may be approximately hemispherical in shape, for example to mimic a human head. FIGS. 9A and 9B show examples of suitable inserts, in this case hemispherical inserts, for use with phantoms, such as a cylindrical phantom in FIG. 9A or a conical phantom in FIG. 9B. The insert may simulate a human head, for example to allow for physical measurements with a depth-helmet, such as for commissioning of the treatment planning system for the Gamma Knife, or other radiotherapy systems.

EXAMPLE

An example phantom and examples of verification studies are described below. These examples are provided for the purpose of illustration only and are not intended to be limiting. Although certain systems, materials and configurations are described, these are only for illustration, and it should be understood that other systems, materials and configurations may also be suitable.

In one example, a panoramic view of 192 Cobalt sources was acquired by exposing Gafchromic films wrapped around the surface of a cylindrical phantom. The centre of the phantom was mounted at the isocenter, with its axis aligned along the longitudinal axis of the couch. The shape and size of the source images were calculated based on design specifications from the manufacturer and compared with the measured panoramic images for the verification of source and collimator configuration. Dose at various points on the surface of the phantom was calculated using the algorithm of the planning system and compared with the dose measured in the film.

A. Panoramic Imaging of the Collimator Configuration

In a radiotherapy system such as the PFX radiosurgery system, a design concept of moving sources and a stationary collimator system, as shown in FIG. 1(a), may be used. In this example, the PFX has eight position-controlled source trays called sectors, each of which holds 24 Co-60 sources spaced over 5 levels or rings, totalling 192 sources in the system. Three different sizes of apertures (e.g., 4, 8, and 16 mm) for each source are machined in one piece of tungsten collimator; therefore, there exist 576 collimating channels on the collimator body. The computer-controlled sectors select one of the planned collimator configurations (e.g., 4, 8, 16 mm or blocked), enabling the use of a single shot with a combination of collimator sizes. A cylindrical phantom to hold GafChromic film is shown in FIG. 1(b). As shown in FIG. 1(c), a phantom may be installed to a Leksel Gamma frame for image registration in the planning system and dose delivery.

In accordance with an aspect of the present disclosure, a phantom, in this example a cylindrical phantom, was designed to mount radiochromic films, such as GafChromic films. The base plate, which is attached to the LCF, holds an acrylic cylinder with an inner diameter of 101 mm, length of 180 mm and thickness of 5 mm as shown in FIG. 1(b). A film may be placed on the inner surface of the cylinder with an insert, such as a solid cylindrical insert, securing the film position. In some embodiments, an outer sleeve may be used when a film needs to be wrapped on the outside of the cylinder. Depending on the number of outer sleeves, multiple film set-ups may be possible. Sleeves not only help to hold the film in place, but may also provide a build-up.

To calibrate the phantom, the phantom installed in the LCF with the CT localizer was CT scanned. Small inaccuracies in the phantom acquired during machining were identified in the planning system after image registration by comparing the position of a set of holes machined on the phantom to design specifications of the phantom. These small inaccuracies were corrected for in the source image modeling. The panoramic views of each source were acquired by exposing GafChromic films wrapped around the surface of the cylindrical phantom (FIG. 1c). With the phantom axis aligned along the longitudinal axis of the couch, a single isocenter (shot) was placed in the centre of the phantom.

B. Film Calibration

A set of EBT Gafchromic films (International Specialty Products, Wayne, N.J., USA) was irradiated following the procedure recommended by the manufacturer. Each piece of film was scanned in landscape orientation using an Epson 1680 (Epson America Inc., Long Beach, Calif., USA) flatbed scanner at 150 dots per inch. The calibration curve was found using the same equations as Devic et al[9] without the double-exposure method.

$$\text{Dose} = b \cdot \text{netOD} + c \cdot \text{netOD}^n \quad (1)$$

where b, c and n are the calibration parameters to be found from the set of calibration films and netOD is the net optical density (OD). The films, placed in the Elekta's ABS dosimetric phantom, were irradiated with 8 different levels of dose (e.g., 0, 0.5, 1.0, 2.0, 3.0, 4.0, 6.0 and 8.0 Gy) using the 16 mm collimator. The standard deviation of intensity over a 5×5 mm² window at the centre of each shot was measured to find the uncertainty of the film calibration. Dose in the sampling area was found to be uniform (within 0.3%) according to the treatment planning system (Leksell Gamma Plan 8.0). Images were imported to an image processing program, in this example developed using MATLAB 7.4.0 (Math Works, Natick, Mass.), to extract the red channel component and to calculate calibration parameters.

C. Modeling of Source Imaging

An example model for calculating source configuration is now described, for the example cylindrical phantom described above. Other models or calculations may be used, for example based on treatment planning calculations, to accommodate other phantoms. Such equations and calculations may be conventionally used for treatment planning, but not for quality assurance, as in the present disclosure.

In this example, eight different sectors and five different rings characterize the source arrangement of the PFX. Whilst sectors divide the group of sources in the circumferential direction, rings divide them in the latitudinal direction designated by angle $\phi$. The rings are stacked and each is positioned at a slightly different angle, $\phi$, and radius, r, relative to the machine isocenter.

Figure 2:
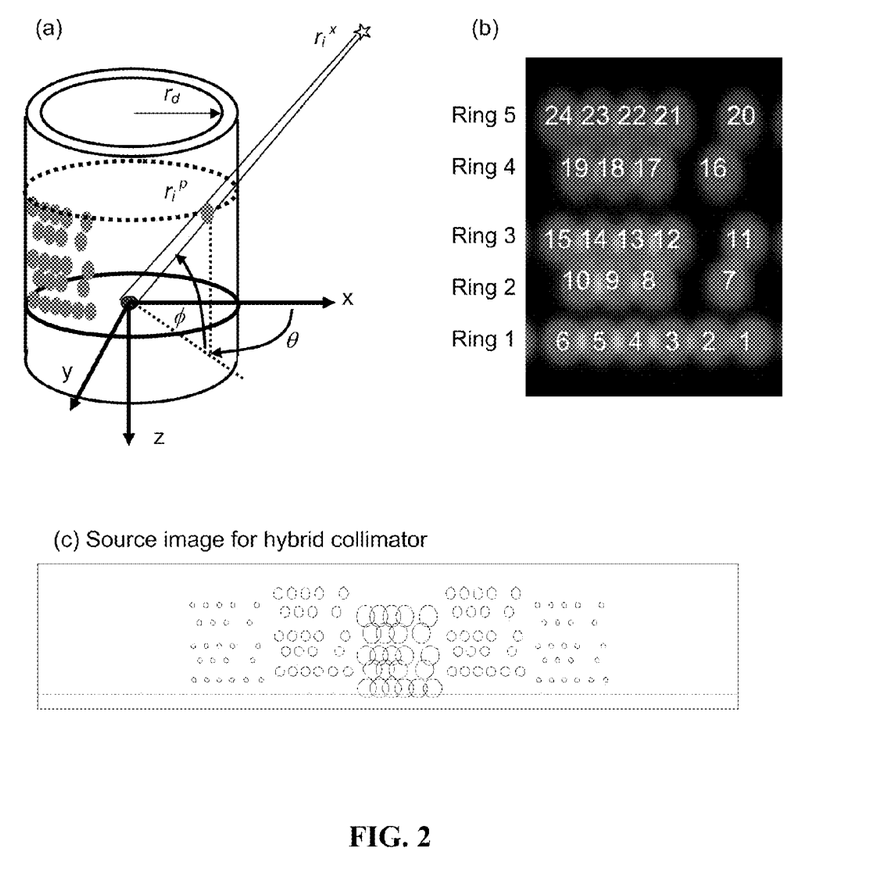
FIG. 2 shows an example phantom and an example panoramic image obtained with the phantom.

FIG. 2 illustrates source imaging on film using a phantom, in this example a cylindrical phantom. The plane of is center (a solid line in (a)) is shown in the horizontal line in (c).

FIG. 2(a) shows the spherical coordinate system to define the source arrangement and depicts the source image from one sector. The upper dotted line shows the latitudinal location of ring number 5 and the lower line shows the plane of the isocenter. The five-ring configuration may be confirmed by five rows of source images as shown in FIGS. 2(b) and (c). Due to the larger latitudinal angle, the source images on the top row (or ring 5) may look more elliptical than those on the bottom row on the film. As shown in FIG. 2(c), a panoramic view of source images for a combination of different collimators (called a hybrid shot), source images from the 16 mm collimators are located closer to the isocenter plane than those from 4 mm collimators. This is because 16 mm collimators are located closer to the front side of the machine (in other words, lower latitudinal angle) than 4 mm and 8 mm collimators, in this example. This may be different for different radiotherapy systems, for example in older versions of GK, the source positions may be coincident due to a stationary source configuration. The position of the centre of the source on the film may be found using the following relationship:

$$r_i^p = \frac{r_d}{\cos(\phi_i^x)} \quad (2)$$
$$\theta_i^p = \theta_i^x$$
$$\phi_i^p = \phi_i^x$$

where $(r, \theta, \phi)_i^x$ is the i-th source position in spherical coordinates, $(r, \theta, \phi)_i^p$ is the position of the source image on the film, $r_d$ is the radius of the phantom and superscripts x and p stand for the source position in space and source image position on film, respectively. i-th source or source identification numbers, i, shown in FIG. 2(b) will be used in the analysis of film dosimetry later.

The diameter of a source image on film, $d_i^p$, may be found considering geometrical beam divergence of the field aperture, d, defined at isocenter for each size of collimator.

$$d_i^p = \left(1 - \frac{r_d}{r_i^x \cos(\phi_i^x)}\right) \cdot d \quad (3)$$

Whilst the diameter of source image along the circumferential direction, $\theta$, of the cylindrical phantom may satisfy equation (3), its latitudinal component, in the direction of $\phi$, may be longer in proportion to the beam angles on the film. The elongated diameter may be approximated by multiplying equation (3) by $1/\cos(\phi_i^x)$. The edge of the beam for each source, i, may be found by creating an ellipse with minor diameter of $d_i^p$ and major diameter of $d_i^p/\cos(\phi_i^x)$ along the circumferential direction, $\theta$, and the axis of the cylinder, $\phi$, respectively. In this example, the curved surface of film may be approximated piece wise flat for the sake of simplification of the modelling.

Using these calculations, the source and/or collimator configuration of the radiotherapy system may be verified, for example by comparing the calculated source configuration with the respective pre-determined intended configuration.

D. Dose Calculation

Example calculations for determining a delivered dosage using the panoramic image is now described. These calculations may be based on conventional equations for treatment planning, and variations may be possible, depending on application.

Figure 3:
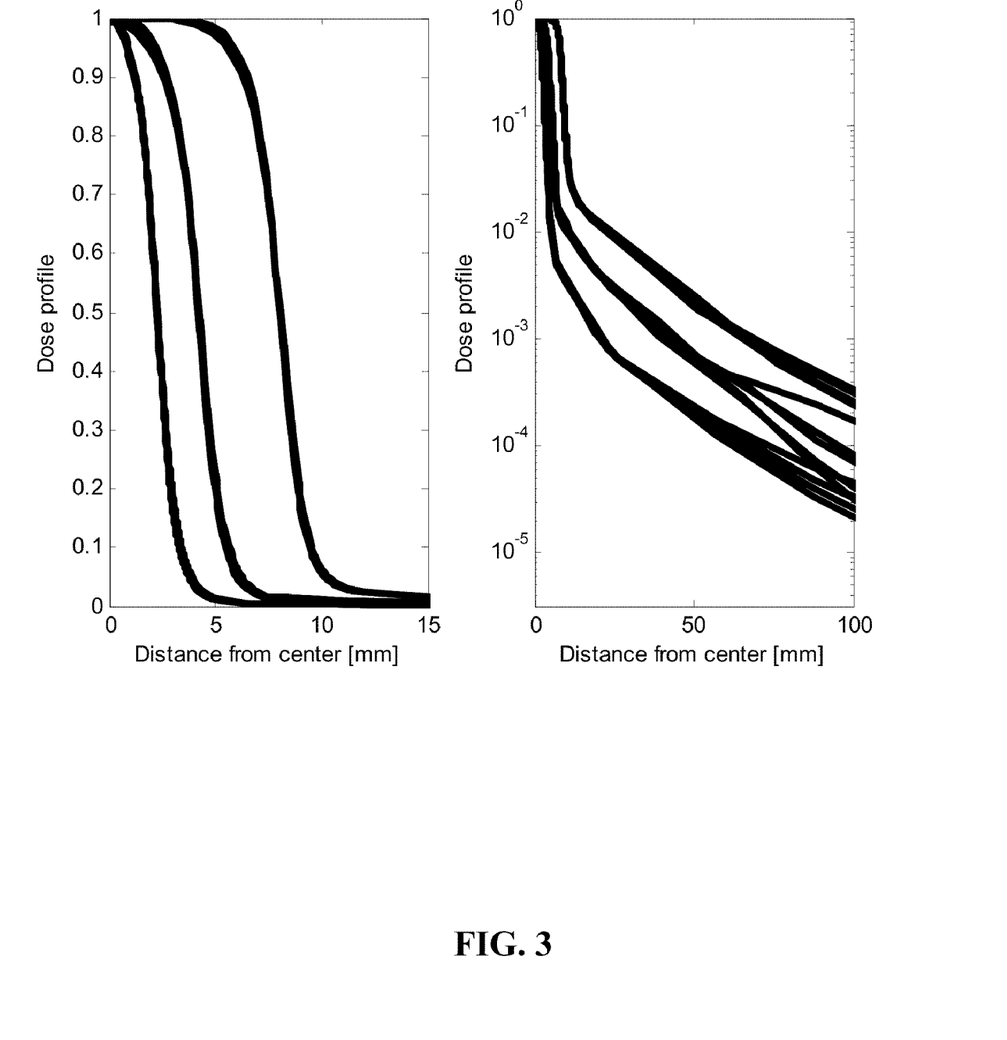
FIG. 3 illustrates example dose profiles reconstructed using known specifications for an example radiotherapy system.

FIG. 3 illustrates example dose profiles using known specifications for the radiotherapy system, in this example using data from the manufacturer for the PFX. Solid line, broken line and dotted line were used for 16 mm, 8 mm and 4 mm collimators respectively.

The dose from source i to any point, j, in the phantom may be found using equation (4). Model parameters are collimator, c, and ring, r.

$$D_i(j) = D_{centre} \cdot ISL \cdot ATT \cdot P^{r,c}(d) \cdot w^{c,r} \bigg/ \sum_{r=1}^{5} n_r w^{c=16,r} \quad (4)$$

w is the output factor normalized to the 16 mm collimator as a function of collimator c, and ring r, ISL is the inverse square law, ATT is the exponential attenuation by the phantom material, $P^{r,c}(x)$ is the dose profile and x is the radial distance from the central axis of the beam. The dose profile $P^{r,c}(x)$ is defined as a function of collimator, ring, and radial distance as shown in FIG. 3. $D_{centre}$ is the dose at the isocenter. Dose to a point can be calculated by adding the dose contribution from all 192 sources (i=1, 2 . . . 192). Dose calculation methods and algorithms, such as those known in the art (e.g., as described in references 11 and 12) may be used for dose calculation.

$$D(j) = \sum_i D_i(j) \quad (5)$$

Dose at the centre of each source image on panoramic film may be computed using equations (4) and (5). The computed dose was compared with the measured dose from the film for the verification of dose model in the planning system. $D_{centre}$ may be known from calibration in this case. The small cylinder with a diameter of 101 mm may be sufficient for source imaging of the 4 mm and 8 mm collimators, resulting in little or no image overlap. The larger cylinder, with a diameter of 152 mm, may be utilized for source imaging of the 16 mm collimator to avoid too much overlap between source images. Prescription doses of 140 Gy, 120 Gy and 100 Gy to the 80 mm radius spherical calibration phantom were delivered with the 4 mm, 8 mm and 16 mm collimators, respectively. About 100 sampling points were taken in a 1 mm radius from each source image centre. The median value was taken to represent the dose of each source. Specialized software (Matlab 7.4.0 (MathWorks, Natick, Mass.)) was for film calibration, registration, modelling of source imaging and dose computation.

Dose on film was averaged over the area of beam entrance from the line of the isocenter-plane (shown in FIG. 2(a)) to 8 cm above it. The average dose on film for each collimator normalized to the prescription dose of 100 Gy to the isocenter was investigated as a measure of peripheral dose from each collimator.

Instead of the verification of dose model described above, the calibration dose at the isocenter, $D_{centre}$, may be calculated from the panoramic image by reformatting the equation (4) and (5) as followings.

$$D_{centre} = \frac{D(j)}{\sum_i ISL \cdot ATT \cdot P^{r,c}(d) \cdot w^{c,r} \bigg/ \sum_{r=1}^{5} n_r w^{c=16,r}} \quad (6)$$

where the dose measured at point j on film is D(j). It may be that the calibration dose at the isocenter, $D_{centre}$, may be linearly proportional to the measured dose. Therefore, the accuracy of dose at the source image may be the same as the accuracy of $D_{centre}$.

Using these or similar calculations, the delivered dosage of the radiotherapy system may be verified, for example by comparing the calculated dosage with the respective predetermined intended dosage. These calculations may be performed for dosages at different locations, including, for example, the isocenter dosage, peripheral dosages and surface dosage.

RESULTS

The panoramic images allowed identification of each of the 192 sources, which may be used to verify their integrity and selected collimator sizes. Scatter and leakage dose contributions from neighbouring sources were calculated at the centre of the source image on panoramic film: 6.3% (ranging from 4.5%-7.4%), 16.7% (12.5%-19.3%) and 66.6% (38%-78%) for the 4 mm, 8 mm and 16 mm collimator respectively. Due to the difference of the scatter and leakage level from each collimator, the dose at the source image in panoramic film may be not simply proportional to output factor but elaborate dose computation algorithm may be used. Film dosimetry of the source images in this example shows good overall agreement with the dose model of the treatment planning system with an accuracy of 0.3% (average) and uncertainty of 4.8% (standard deviation). The average dose on the film surface at the beam entrance was 23.96 cGy, 60.76 cGy and 186.2 cGy for a single shot of each collimator: 4 mm, 8 mm and 16 mm, when a dose of 100 Gy was prescribed to isocenter.

A. Panoramic Imaging of the Collimator Configuration

Figure 4:
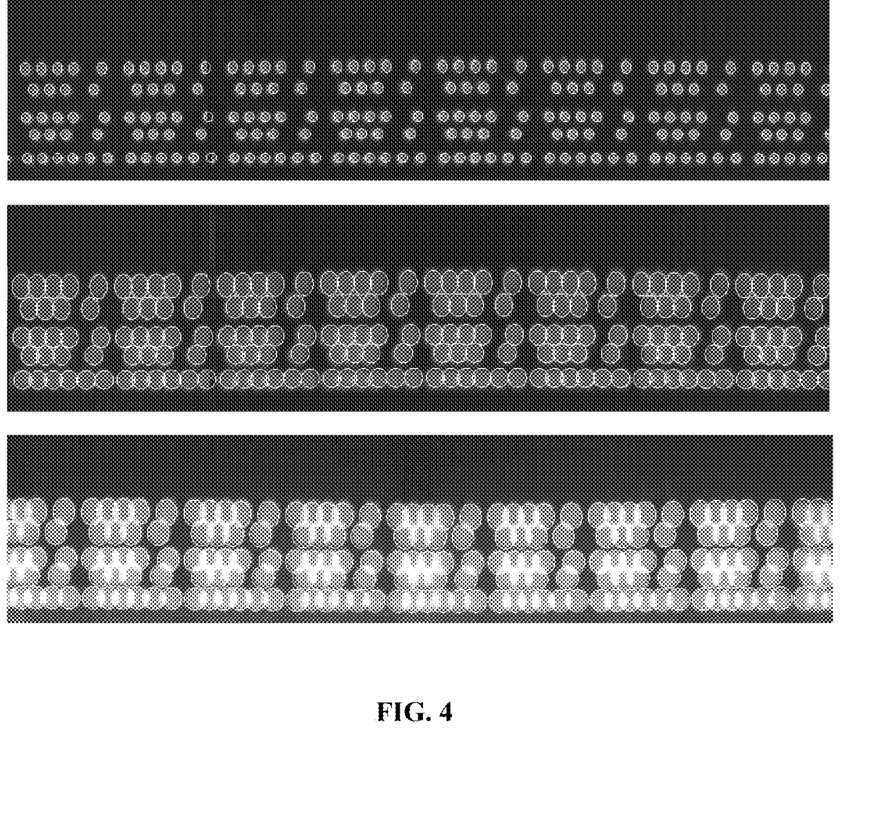
FIG. 4 shows example panoramic images obtained using the example phantom of FIG. 1.

FIG. 4 shows example of panoramic images showing each collimator configuration. Tilt and miss-alignment of phantom (<0.2° and <0.4 mm) with respect to Leksell Coordinate System was compensated. Elongated source image with larger latitudinal angle, φ, is visible and matched well with numerical model.

In this example, the panoramic image allowed identification of each of the 192 sources, which may be used to verify their integrity and selected collimator sizes. Design specifications of source and collimator geometry were verified by using the numerical models described in equations (2) and (3). The source boundaries shown by the white lines in FIG. 4 were calculated from the geometrical model with a phantom location correction as shown on top of the source images and are well matched. The higher the ring number in the superior direction, the more elliptical the source shape is; this is expected due to the increasing beam angle. The larger phantom was used for the 16 mm collimator for clear separation of each source. Careful inspection of the images shows that the source images of each ring are not aligned to a straight line but follow a low amplitude sinusoid (not shown in figure). This may be due to the shift in phantom location from design specifications. An accuracy of less than 0.3 degrees of tilt and 4 mm shift of the phantom relative to the design specification was identified from the CT study in the planning system (LGP v 8.0). These inaccuracies due to phantom machining were compensated for in equations (2) and (3) by shifting and rotating the source positions $(r, \theta, \phi)_i^x$ relative to the new phantom coordinate.

B. EBT Gafchromic Film Calibration

Figure 5:
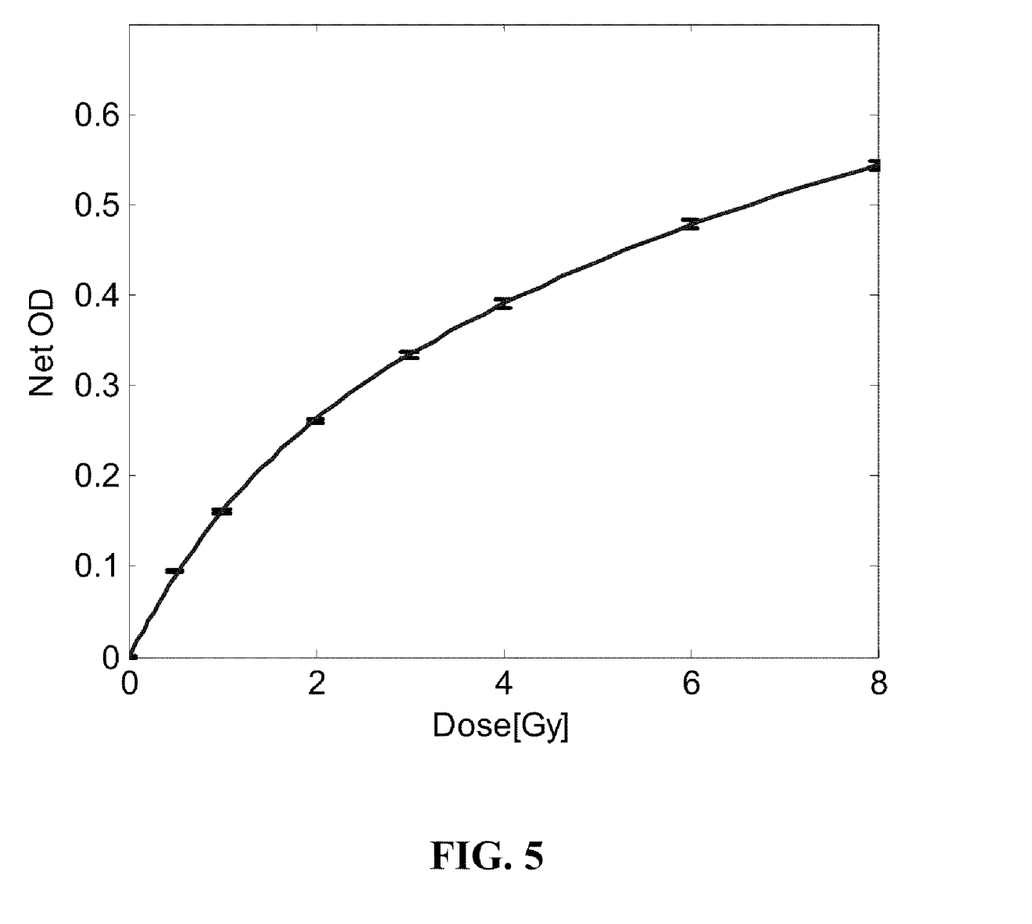
FIG. 5 illustrates example of a film dose calibration curve.

FIG. 5 illustrates an example of calibration of a panoramic image obtained using a phantom. In this example, the GafChromic film was calibrated using Devic's equation. Total relative uncertainty for dose measurement is estimated to be 3.1% for dose larger than 100 cGy. The calibration parameters used in this study are b=5.330, c=30.502, and n=2.934.

29×29 sampling-points were acquired in the measurement window of 5×5 mm² at the centre of each shot. Median netOD and standard deviation of netOD in the measurement window were found from three different experiments. Standard deviations of netOD agreed within 2% of the median OD in each measurement film. Dose uncertainty analysis was performed adapting the procedures proposed by Devic et al[9]. Total relative uncertainty for dose measurement is estimated to be 3.1% for doses larger than 100 cGy. The calibration parameters used in this study are b=5.330, c=30.502, and n=2.934. FIG. 5 shows the calibration curve with error bars for netOD measurement with one standard deviation of uncertainty.

C. Dose Measurement

Figure 6:
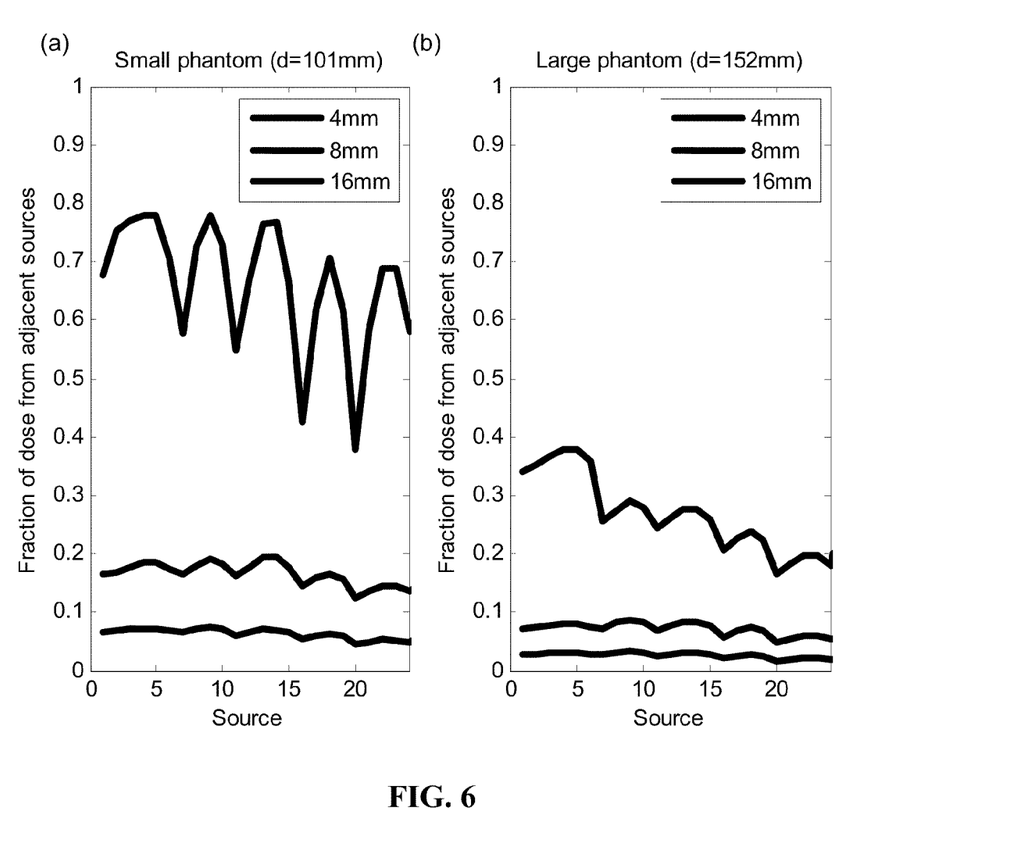
FIG. 6 illustrates example of dose contribution from neighbouring sources.

Dose calculated at each source image using the dose model in equations (4) and (5) included the dose contribution not only from its own source but also from other sources. Given the phantom setup, the fraction of dose contributed by other sources was found to be 6.3% (ranging from 4.5%-7.4%), 16.7% (12.5%-19.3%) and 66.6% (38%-78%) for the 4 mm, 8 mm and 16 mm collimators, respectively when using the small phantom. It was 2.7% (1.7%-3.3%), 7.15% (4.7%-8.8%) and 26.7% (16.5%-37.9%) for 4 mm, 8 mm and 16 mm collimators respectively when using the larger phantom as shown in FIG. 6. The reduction of neighbour dose with the large phantom may be due to the larger separation of sources on the panoramic image. Although dose at the isocenter may be simply proportional to the output factor of the collimator (0.805, 0.924, 1.0) for the same irradiation time, dose at the distance from isocenter in the panoramic view may be complex due to the varying amount of dose contribution from other sources as shown in FIG. 6. Full utilization of dose model may be used to calculate dose on source image as described above. This may allow verification of the accuracy of the dose model in planning system and also may allow calculation of calibration dose at the isocenter from panoramic imaging. Typically, larger separation and increased distance from the isocenter may reduce the dose contribution from neighboring sources for larger phantom.

Figure 7:
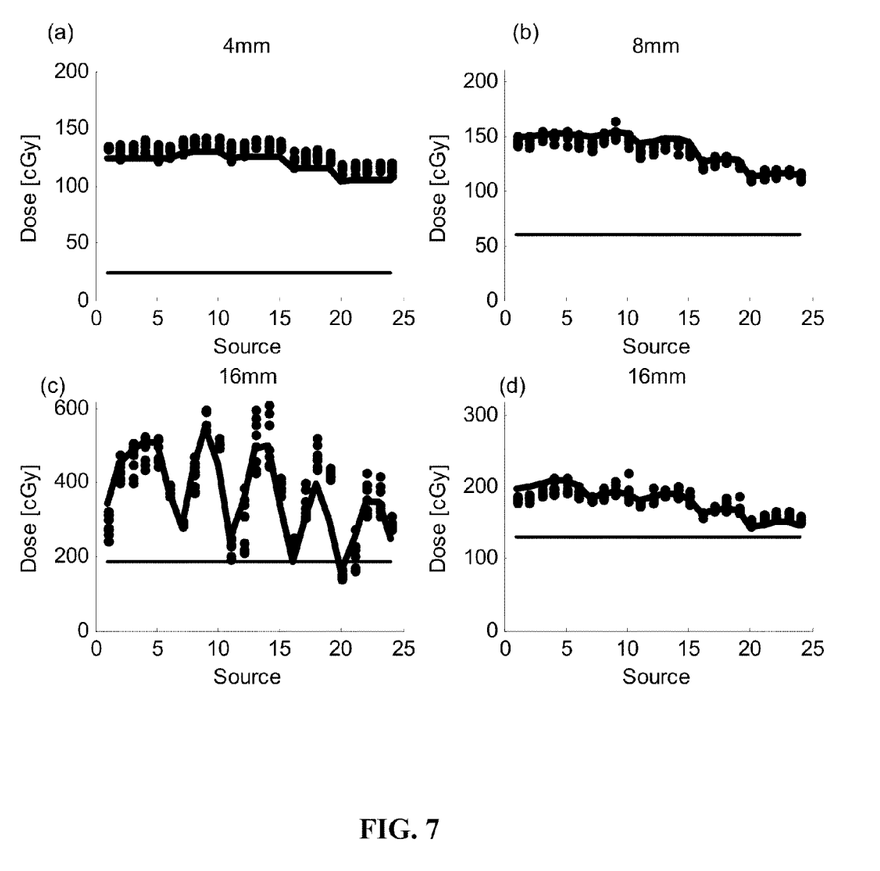
FIG. 7 illustrates example of dose to radiochromic film at the center of panoramic images for each source in an example radiotherapy system.

Dose at each source image measured from films were compared with the dose model. FIG. 7 shows dose to the film at the center of source images for each collimator. The film dose is normalized to the prescription dose of 100 Gy to the spherical phantom with 8 cm radius.

Good overall agreement was observed between the film measurement and the dose model with an accuracy of 0.3% on average and standard deviation of 4.8%. FIG. 7 shows computed dose in solid line and measured dose in solid circle when 100 Gy is delivered to the isocenter of the spherical phantom for easy comparison. In each source number, there are eight measurement points from each sector. Average dose was under-estimated by 2.4% for the 4 mm collimators and over-estimated by 3.4% for the 8 mm collimators. Large variation is observed for 16 mm collimator at small phantom due to the multiple overlap with edge of neighbour source image. Free of overlap with larger phantom reduced measurement variation significantly as shown in FIG. 7(d). Average dose on the cylindrical film surface in the area of beam entrance was 23.96 cGy, 60.76 cGy and 186.2 cGy for a single shot of each collimator, 4 mm, 8 mm and 16 mm. The average doses on film are shown in thin dashed lines in FIG. 7. The ratios of average dose for 8 mm/4 mm and 16 mm/4 mm collimators were therefore 2.537 and 7.774, respectively. They were 2.328 and 6.888 for larger phantom. This means that 2.537 times more entrance dose may be given at the surface of small phantom when single shot of 8 mm collimator is used compared to single shot of 4 mm collimator to deliver the same maximum dose.

Figure 8:
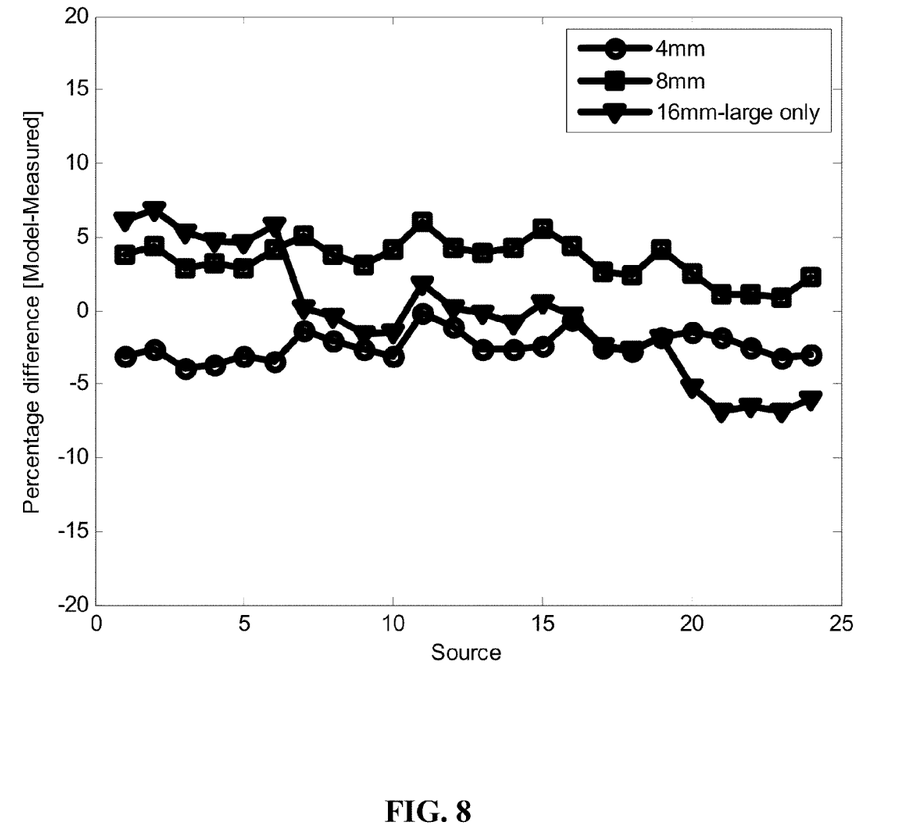
FIG. 8 illustrates an example of comparison between measured dose and dose model.

FIG. 8 shows the percentage difference of measured dose from dose model (dose from model—dose from measurement) as a function of source number. In this example, the film dose is normalized to the prescription dose of 100 Gy to the spherical phantom with 8 cm radius. A weak trend was observed as a function of source (or ring) for the 16 mm collimator. However, the variation may be within an acceptable small range.

$D_{centre}$ was calculated as described in section III.D from the panoramic source image. It was over-estimated by 2.4%, under-estimated by 3.4% and under-estimated by 0.2% for a single shot of each collimator, 4 mm, 8 mm and 16 mm.

DISCUSSION

Source and collimator modules are enclosed in the some models of radiotherapy systems, such as models of Gamma Knife, and this design may make validation of integrity of the system more challenging. By obtaining a panoramic image, each individual source may be visualized and the dose of each source may be measured on film. The existence of sources and their relative source activity may be obtained from the panoramic image. This may provide a way to check the sources and collimator arrangement during the commissioning process. Film dosimetry on a panoramic image may provide another way to validate the dose computation algorithm used in the treatment planning system. In examples and experiments, an agreement of less than 3.6% difference between the measured dose and calculated dose was obtained. Considering the measured dose on film is no more than 6% of the prescription dose for 16 mm (FIG. 7c) and only 1.2% for 4 mm collimator (FIG. 7a), the measurement uncertainty relative to the prescription dose may be considered acceptably small.

Devic et al[9] showed that the dosimetric uncertainty for uniform fields could be 2% or less for doses above around 0.4 Gy in case of the EBT. Fiandra et al[10] introduced a correction factor for a light scattering effect for large film dosimetry and eliminated the double exposure required in the Devic's study in order to save time and to decrease uncertainties from coregistration errors.

In some examples and experiments, correction factors, depending on the location in the film and delivered dose, ranged from 0.9 to 1.0 for uniformly exposed films with doses between 0 and 500 cGy. Larger corrections may be required when using higher doses at the edge of the film. In the disclosed examples, source images on the panoramic view were located central to the film where minimum correction was required and relatively small average dose was delivered (average dose is less than 130 cGy for small phantom experiment). Thus, the effect of light scatter correction on the panoramic view may be assumed to be small for small collimator and thus this correction factor was not applied in this study. A weak trend of under-estimation along the higher ring for the 16 mm collimator might be due to the light scattering effect, however. Further calibration may reduce the uncertainty of the dose measurement further.

The design of certain models of radiotherapy systems, such as the LGK PFX, may allow the fractionated radiotherapy of larger volumes using a relocatable frame. Peripheral dose to healthy tissue outside of the intended target in LGK treatment is of great interest recentlyl[15-17]. Ma et al.[16] compared characteristics of dose fall off for CyberKnife, LGK and linear accelerators with micro multi-leaf collimators (MLCs). Characteristics of peripheral dose from each collimator, therefore, may help to understand dose fall off. Recently, a power law relationship between irradiation time and target size has been reported[15]. In that report, it was demonstrated that delivering the same dose to a given spherical target, the irradiation time with 4 mm collimators was 3.5 and 12.5 times of that with 8 mm and 16 mm collimators, respectively. When all the shots were placed in the isocenter, the isocenter dose with 4 mm collimator became 3.0 and 10 times of that with 8 mm and 16 mm collimators, respectively, considering output factors (0.805, 0.924, and 1.0 for the 4 mm, 8 mm, 16 mm collimators). Since the average entrance dose with 4 mm collimator is 1/2.537 and 1/7.774 times of that with 8 mm and 16 mm collimators for the same isocenter dose, the average dose on film would increase when smaller collimators replaces larger collimators to deliver the same dose to a given spherical target. Since peripheral dose varies as a function of latitudinal angle, other clinical factors such the location of critical organ, and treatment efficiency may also affect the choice of collimator combination in practice.

In the disclosed examples, using cylindrical phantoms, panoramic view of source imaging may provide the surface dose information on the cylindrical phantom. Surface dose in the area of beam entrance may be similar to fluence measurement in the intensity modulated radiation therapy, which is one of the most frequently used patient specific quality assurance tests. Thus panoramic imaging technique may be utilized for a patient-specific QA of radiotherapy treatment by comparing the surface dose in the area of beam entrance (i.e., fluence) with the fluence computed from planning system. This verification may be useful for assuring treatment plan quality for radiotherapy, for example using Gamma Knife.

Care was taken during the positioning, marking, scanning, registration, and calibration of the film for an accurate experiment especially with the 4 mm collimator. In some examples, two sheets of film were stitched together for one set of measurements in our study. A few dose measurement points close to the edge of the film were discarded from the analysis due to increased uncertainty.

In some examples, a registration method may be used to register the position of the detector surface in relation to the phantom and/or the system. For example, the phantom may include a reference mark (e.g., a lead bead) that is imaged by the detector surface to serve as a reference point on the panoramic image.

APPLICATIONS

The disclosed methods and phantoms may provide a way to verify the integrity of a radiotherapy system, such as LGK PFX or the Cyber Knife system. The disclosed methods and phantoms may also be used for verification in other radiation treatment systems, including, for example, linear accelerator and tomotherapy systems. Although the examples mainly discuss the PFX, the methods and systems disclosed may also be applied to other radiotherapy systems, even those without the calibration and verification challenges encountered with the PFX. For fractionated radiation therapy using a relocatable frame at PFX, panoramic imaging may be equivalent to using fluence map QA in intensity modulated radiation therapy using a linear accelerator.

The disclosed methods and phantoms may be useful for verification of source and/or collimator configuration and integrity. This verification may be performed when the system is initially installed, as part of regular maintenance, or as part of the setup for treatment of a patient.

In some examples, for verification of radiotherapy systems having multiple individual sources, the phantom may be configured to allow simultaneous testing of source type and source strength. For example, source type may be determined using two or more layers of detector surfaces (e.g., through the use of nesting sleeves as described above) during a single exposure of the phantom. For example, source strength comparisons may be done for a single detector surface or for multiple nested detector surfaces. Where multiple nested detector surfaces are used, this may also provide a measure of the source percent depth dose, which is a common quality assurance test.

The disclosed methods and phantoms may allow for determination and/or evaluation of dosage at the isocenter and/or of peripheral dose in areas peripheral to the isocenter. Determination of dosage at the isocenter may be used in place of or to verify measurements from a radiation detector located at the isocenter of the system.

The disclosed methods and phantoms may be useful for validation of a dose calculation algorithm used by the treatment planning system. For example, verification of a treatment plan may be carried out by delivering the planned treatment to the phantom, and calculating the actual dosage delivered using the obtained panoramic image. The calculated actual dosage may be compared to the planned dosage in order to validate the treatment plan. The obtained panoramic image may also be compared to a calculated expected image in order to validate the treatment plan. This verification may provide advantages over conventional verification using a detector located at the isocenter because the panoramic image allows for more detailed calculations about the geometry of the delivered dosage, including any peripheral dose. Conventional verification methods may be limited to a point or 2D determination of delivered dosage at the isocenter.

Panoramic images may be obtained just prior to treatment of a patient, for example as part of the system setup. This may be for verification of the system configuration and/or verification of a treatment plan for the patient. Verification of a treatment plan immediately prior to actual treatment may be based on an accelerated or abridged treatment plan, using more sensitive surface detectors, and may be in addition to more thorough verification of the treatment plan done ahead of time. Panoramic images obtain from such pre-treatment verification may be recorded or stored as part of the patient file, for example, to provide traceability and accountability.

The embodiments of the present disclosure described above are intended to be examples only. Those of skill in the art may effect alterations, modifications and variations to the particular embodiments without departing from the intended scope of the present disclosure. In particular, selected features from one or more of the above-described embodiments may be combined to create alternative embodiments not explicitly described, features suitable for such combinations being readily apparent to persons skilled in the art. The subject matter described herein and in the recited claims intends to cover and embrace all suitable changes in technology. All references mentioned are hereby incorporated by reference in their entirety.

REFERENCES

1. J. C. Flickinger, D. Kondziolka, L. D. Lunsford, R. J. Coffey, M. L. Goodman, E. G. Shaw, W. R. Hudgins, R. Weiner, G. R. t. Harsh, P. K. Sneed, and et al., "A multi-institutional experience with stereotactic radiosurgery for solitary brain metastasis," Int J Radiat Oncol Biol Phys 28, 797-802 (1994).
2. D. A. Larson, et al., "Gamma knife for glioma: selection factors and survival," *Int. J. Radiat. Oncol. Biol. Phys.* 36 1045-1053 (1996).

3. S. K. Seung, et al., "Gamma knife radiosurgery for malignant melanoma brain metastases," *Cancer J. Sci. Am.* 4 103-109 (1998).
4. J. Régis, P. Metellus, M. Hayashi, P. Roussel, A. Donnet, and F. Bille-Turc, "Prospective controlled trial of gamma knife surgery for essential trigeminal neuralgia," J Neurosurg 104, 913-924 (2006).
5. D. Kondziolka D, J. G. Ong, J. Y. Lee, R. Y. Moore, J. C. Flickinger, and L. D. Lunsford, "Gamma Knife thalamotomy for essential tremor," J Neurosurg 108 (1) 111-117 (2008).
6. C. Lindquist, and I. Paddick, "The Leksell Gamma Knife Perfexion and Comparisons with its Predecessors," Neurosurgery 61, 130-141 (2007)
7. J. Régis, M. Tamura, C. Guillot, et al. "Radiosurgery with the world's first fully robotized Leksell Gamma Knife Perfexion in Clinical use: A 200-patient prospective, randomized, controlled comparison with the Gamma Knife 4C," Neurosurgery 64, 346-356 (2009)
8. A. H. Maitz, A. Wu, L. D. Lunsford, J. C. Flickinger, D. Kondziolka, W. D. Bloomer, "Quality assurance for gamma knife stereotactic radiosurgery," Int J Radiat Oncol Biol Phys 32, 1465-1471 (1995).
9. S. Devic, J. Seuntjens, E. Sham, E. B. Podgorsak, C. R. Schmidtlein, A. S. Kirov, and C. G. Soares, "Precise radiochromic film dosimetry using a flat-bed document scanner," Med Phys 32, 2245-2253 (2005).
10. C. Fiandra, U. Ricardi, R. Ragona, S. Anglesio, F. R. Giglioli, "Clinical use of EBT model Gafchromic™ film in radiotherapy," Med. Phys. 33, 4314-4319 (2006)
11. Online Reference Manual, Leksell GammaPlan® 8.0, Document number 1003197 Rev. 01(2006/12)
12. Leksell GammaPlan® 8.0 Reference Documents, Art. Number. 1003135 Rev 1
13. C. Yu, G. Luxton, M. L. Apuzzo, D. M. MacPherson, Z. Petrovich, "Extracranial radiation doses in patients undergoing gamma knife radiosurgery," Neurosurgery 41, 553-560 (1997).
14. S. M. Marcu, Q. J. Wu, K. Pillai, and M. S. Weinhous, "GammaPlan®-Leksell Gamma Knife® radiosurgery treatment planning verification method," Med. Phys. 27, 2146-2149 (2000).
15. M. Ruschin, H. Nordström, P. Kjäll, Y. B. Cho and D. Jaffray, "Investigation of intra-cranial peripheral dose arising from the treatment of large lesions with Leksell GammaKnife® Perfexion™," Med. Phys. 36. 36, 2069-2073 (2009).
16. L. Ma, A. Sahgal, M. Descovich, Y. B. Cho, C. Chuang, K. Huang, N. J. Laperriere, D. Shrieve, D. A. Larson, "Equivalence in Dose Fall-off for Isocentric and Non-isocentric Intracranial Treatment Modalities and its Impact on Dose Fractionation Schemes," *Int. J. Radiat. Oncol. Biol. Phys* under review
17. L. Ma, L. Verhey, C. Chuang, M. Descovich, V. Smith, K. Huang, M. McDermott and P. Sneed, "Effect of composite sector collimation on average dose fall-off for Gamma Knife Perfexion," J Neurosurg 109, 15-20 (2008).
18. M. C. Schell, F. J. Bova, D. A. Larson, D. D. Laevitt, W. R. Lutz, E. B. Podgorsak, and A. Wu, Stereotactic Radiosurgery, Report of Task Group 42 Radiation Therapy Committee, (American Institute of Physics Inc., Woodbury, 1995)
19. Y-B Cho, M. van Prooijen, D. A. Jaffray, M. K. Islam "Verification of source and collimator configuration for Gamma Knife Perfexion using panoramic imaging," Med. Phys. 37(3), 1325-1331 (2010)

The invention claimed is:

1. A phantom for verification in a radiotherapy system comprising:
    a hollow body configured to support a detector surface for obtaining a panoramic image of individual radiation beams produced by one or more sources in the radiotherapy system; and
    at least one of:
        an outer sleeve positionable about an outer surface of the body, for conforming the detector surface to an outer geometry of the body; and
        a solid inner core positionable inside the body, for conforming the detector surface to an inner geometry of the body;
    wherein the body is configured to position the detector surface for obtaining the panoramic image in an intermediate region between the one or more sources and a target isocenter of the radiotherapy system.

2. The phantom of claim 1 wherein the body is configured to support the detector surface for obtaining the panoramic image of all radiation beams produced by one or more sources in the radiotherapy system.

3. The phantom of claim 1 wherein the body is configured to support the detector surface in at least partially a substantially cylindrical, conical, cubical or spherical geometry.

4. The phantom of claim 1 wherein the body is configured to a support the detector surface that is one of: a radiation detecting film, a fluorescent screen and a solid state screen.

5. The phantom of claim 1 comprising a plurality of nesting outer sleeves.

6. The phantom of claim 1 wherein the body has a cylindrical, conical, cubical or spherical geometry.

7. The phantom of claim 1 comprising an insert for depth-helmet measurements.

8. The phantom of claim 1 wherein the panoramic image is produced by at least one of individual entrance beams towards the phantom and individual exit beams away from the phantom.

9. The phantom of claim 1 wherein the body is configured to position the detector surface to at least partially surround the target isocenter.

10. A method of verification in a radiotherapy system, the method comprising:
    obtaining a panoramic image of individual radiation beams in the radiotherapy system, the panoramic image being indicative of locations of individual beams produced by one or more sources in the radiotherapy system; and
    calculating source configuration of the one or more sources, based on the beam images of the panoramic image, for verification with a pre-determined target configuration.

11. The method of claim 10 wherein the panoramic image is obtained in an intermediate region between the one or more sources and a target isocenter of the radiotherapy system.

12. The method of claim 11 wherein the panoramic image is obtained from a surface at least partially surrounding the target isocenter.

13. The method of claim 10 wherein the calculated radiation dosage comprises at least one of: an isocenter dosage, a peripheral dosage, and a surface dosage.

14. The method of claim 10 wherein the calculated source configuration comprises at least one of: source location and collimator configuration.

15. The method of claim 10 further comprising obtaining a dosage measurement at a target isocenter of the radiotherapy system.

16. The method of claim 10 wherein the panoramic image is obtained for a surface having at least partially a substantially cylindrical, conical, cubical or spherical geometry.

17. The method of claim 10 wherein the radiotherapy system comprises a single movable radiation source.

18. The method of claim 10 wherein the panoramic image is obtained using a detector surface.

19. The method of claim 18 wherein the detector surface is one of: a radiation detecting film, a fluorescent screen and a solid state screen.

20. The method of claim 10 wherein calculating the source configuration is carried out substantially in real-time with obtaining the panoramic image.

21. The method of claim 10 wherein the panoramic image is produced by at least one of individual entrance beams towards a target isocenter of the radiotherapy system and individual exit beams away from the target isocenter.

22. The method of claim 10 wherein obtaining the panoramic image comprises:

providing a phantom and a detector surface in a treatment area of the radiotherapy system;

wherein the phantom comprises:

a body configured to support the detector surface for obtaining a panoramic image of individual radiation beams produced by the one or more sources in the radiotherapy system;

wherein the body is configured to position the detector surface for obtaining the panoramic image in an intermediate region between the one or more sources and a target isocenter of the radiotherapy system; and applying radiation beams to the detector surface.

23. The method of claim 10 further comprising calculating radiation dosage based on the beam images of the panoramic image, for verification with a pre-determined target dosage.

24. The method of claim 23 wherein calculating the radiation dosage is carried out substantially in real-time with obtaining the panoramic image.

* * * * *